United States Patent [19]

Saksena et al.

[11] Patent Number: 5,462,544
[45] Date of Patent: Oct. 31, 1995

[54] CONTINUOUS HEART TISSUE MAPPING AND LASING CATHETER

[75] Inventors: Sanjeev Saksena, Green Brook, N.J.; Stanislaw Sulek, Anaheim; Hany M. G. Hussein, Costa Mesa, both of Calif.

[73] Assignee: Energy Life System Corporation, Costa Mesa, Calif.

[21] Appl. No.: 57,735

[22] Filed: May 5, 1993

[51] Int. Cl.$^6$ ............................. A61B 17/36; A61B 5/04
[52] U.S. Cl. ............................. 606/15; 128/642
[58] Field of Search ............................. 128/642; 606/15, 606/16

[56] References Cited

U.S. PATENT DOCUMENTS

| | | | |
|---|---|---|---|
| 4,777,955 | 10/1988 | Brayton et al. | 128/642 |
| 4,785,815 | 11/1988 | Cohen | 128/642 |
| 5,032,123 | 7/1991 | Katz et al. | 606/15 |
| 5,104,393 | 4/1992 | Isner et al. . | |
| 5,111,832 | 5/1992 | Saksena . | |
| 5,140,987 | 8/1992 | Schuger et al. | 128/642 |
| 5,154,501 | 10/1992 | Svenson et al. . | |
| 5,172,699 | 12/1992 | Svenson et al. . | |
| 5,242,441 | 9/1993 | Avitall | 128/642 |

FOREIGN PATENT DOCUMENTS

| | | | |
|---|---|---|---|
| 3814847 | 11/1989 | Germany | 128/642 |
| 2017506 | 10/1979 | United Kingdom | 606/15 |

OTHER PUBLICATIONS

Saksena, Pace 12: 196–203 (1989).

*Primary Examiner*—Lee S. Cohen
*Attorney, Agent, or Firm*—Olson & Hierl, Ltd.

[57] ABSTRACT

A heart tissue mapping and lasing catheter well suited for control of tachyarrhythmias is disclosed. A distal end region of the catheter has an electrode envelope constituted by plural surface electrode pairs spaced from one another and is provided with at least one fiber optic within the electrode envelope. The emissive face of the fiber optic is situated between adjacent electrode pairs in the electrode envelope.

17 Claims, 6 Drawing Sheets

5,462,544

CONTINUOUS HEART TISSUE MAPPING AND LASING CATHETER

TECHNICAL FIELD

This invention relates to catheters suitable for in vivo mapping of heart muscle and ablation of diseased heart tissue. The present catheters are particularly well suited for control of tachyarrhythmias.

BACKGROUND OF THE INVENTION

One type of tachyarrhythmia is ventricular fibrillation - an irregular and uncoordinated action of heart muscle fibers. The result of such action is a failure or impairment of the heart to pump blood.

Ventricular tachycardia is another type of tachyarrhythmia and is also an irregularity of the heart muscle, generally characterized by an abnormally fast and altered contraction pattern, which may in some instances itself lead to death in a few minutes. Supraventricular tachycardia occurs in the tissues of the heart above the ventricles, especially in the sinus node, the atrium, the atrioventricular (AV) bypass tract, or in the AV node. Such tachycardias, especially ventricular tachycardia, are subject to being accelerated into ventricular fibrillation by a number of known factors and stimuli, and hence their existence poses a latent or overt threat to continued life.

The importance of the foregoing is that ventricular tachycardia may, and ventricular fibrillation does, result in cessation of adequate pump function of the heart and sudden cardiac death. This is the leading cause of death of humans in the United States.

Various therapeutic means for controlling tachyarrhythmias have evolved. These include pharmaceutical compounds and compositions for suppressing tachyarrhythmias, implantable antitachycardia devices, and mechanical surgical procedures for the resection (removal by cutting) of heart tissue. Cardiac mapping techniques conducted during sinus rhythm and/or during induced tachycardia have made possible the identification of specific zones of heart tissue which are the foci of tachyarrhythmias. Such foci occur in many portions of the heart tissue, varying from person to person, and in normal tissue as well as in diseased tissue. Thus, cardiac mapping is an almost necessary diagnostic technique preceding the practice of the inventions set forth herein, but is to be performed on each patient on a case-by-case basis.

Although cardiac mapping has greatly improved the identification of the location of the foci of tachyarrhythmias, thus improving the success of mechanical resection surgery, most such foci occur where mechanical resection is difficult or impractical to perform. Alternative means for the ablation of tissue containing tachyarrhythmia foci have been attempted, e.g., cryothermia, and electrical energy delivered by means of electrode-bearing catheters. However, the therapeutic efficacy of electrical energy for treating ventricular tachycardia is still subject to debate among surgeons and physicians.

It would be desirable to have a device and method for ablation of diseased heart tissue that can be continuously monitored while in use, and that can be applied to the heart tissue in locations that are not readily resectable by current methods.

The present invention satisfies the foregoing desires, and provides for the control of tachyarrhythmias in living humans by ablating tissue in vivo by subjecting the heart tissue at a selected site to a laser beam having sufficient energy and for a sufficient time to create a focal lesion at such site. The site in question can be within an area on the inner or outer surface of heart tissue which has been previously located by cardiac mapping as causing an arrhythmia. For example, the site may be on the inside or the outside of a heart's ventricle or atrium, or in the atrioventricular groove. To effect ablation, the laser energy is transmitted as a beam and precisely directed to the selected site for direct impingement by means of an elongated thin optical fiber or fiber optic. The laser energy can be emitted in a series of short discrete pulses or continuously.

SUMMARY OF THE INVENTION

The present invention provides a mapping and lasing catheter capable of continuously performing both of the aforesaid functions and methods for using such catheter. Concurrent mapping of tissue and diseased tissue ablation permit continuous monitoring of the medical procedure as the procedure is performed, as well as effective control of laser irradiation dosimetry during the procedure.

The contemplated continuous mapping and lasing catheter is suitable for intraoperative and percutaneous application. The catheter is provided at a distal end region thereof with an electrode envelope that is constituted by plural surface electrode pairs spaced from one another. The surface electrodes can be continuous bands that circumscribe the catheter, or they can be discontinuous lands or regions on the peripheral catheter surface.

At least one fiber optic is provided within said electrode envelope and is situated to direct a laser beam at a tissue target site that is adjacent to the electrode envelope. The fiber optic is positioned with its emissive face between adjacent electrode pairs in the electrode envelope. In this manner the diseased tissue region can be precisely located and subsequently effectively ablated.

DESCRIPTION OF PREFERRED EMBODIMENTS

Figure 1:
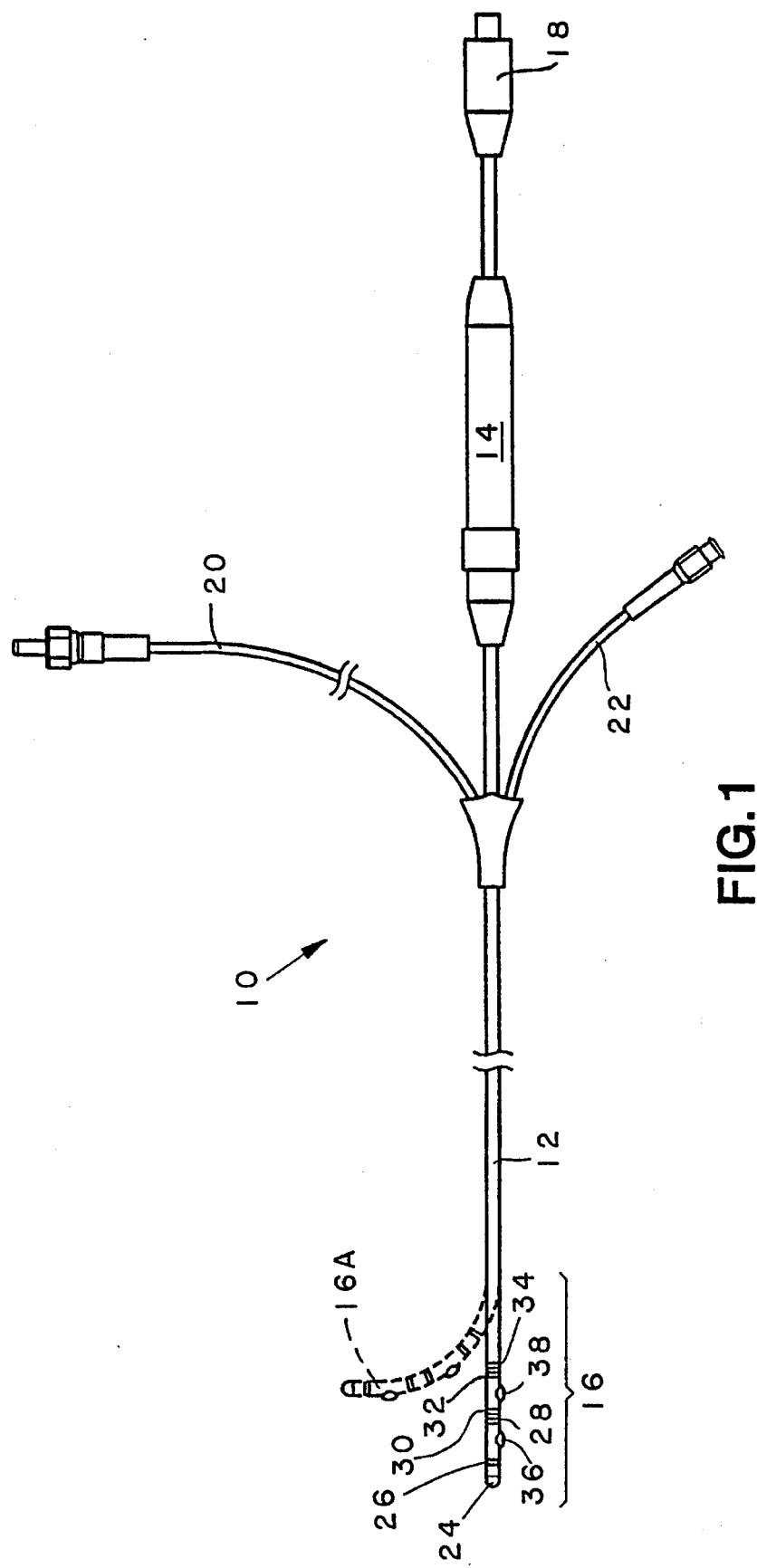
FIG. 1 is a fragmentary overall view of a tissue ablating catheter that embodies the present invention.

Referring to FIG. 1, continuous mapping and lasing catheter 10 comprises tubular catheter body 12 having a deflectable distal end region 16, manipulating handle 14, connector plug 18, fiber optic conduit 20, and flushing liquid conduit 22. Distal end region 16 in a deflected position is shown in phantom as distal end region 16A. Electrode pairs 24, 26; 28, 30; and 32, 34 together define an electrode envelope within which are situated fiber optics with emissive end faces 36 and 38. Preferably, the fiber optics and their respective associated end faces 36 and 38 are positioned so that upon deflection of the distal end region 16 the end faces 36 and 38 remain on the outer curvature of the resulting bend as shown in FIG. 1.

Figure 2:
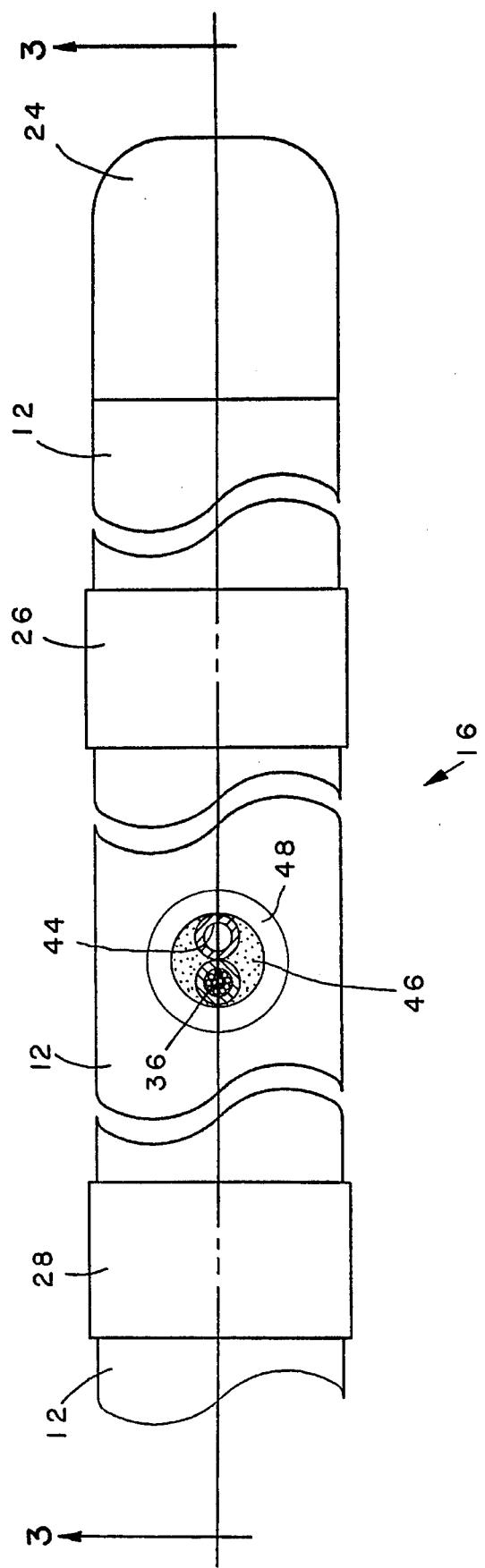
FIG. 2 is an enlarged fragmentary view of a distal end region of a catheter embodying the present invention.
Figure 3:
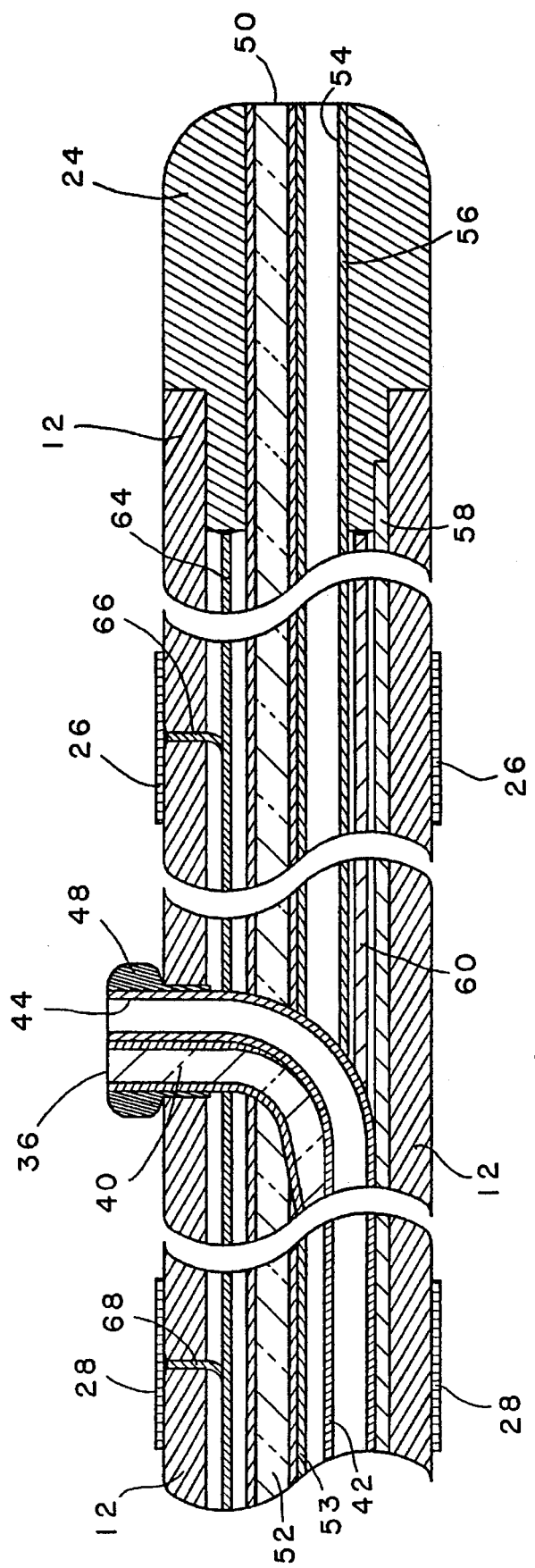
FIG. 3 is a sectional elevation of the distal end region shown in FIG. 2 and taken along plane 3—3 in FIG. 2.

Distal end region 16 is shown in greater detail in FIGS. 2 and 3. Catheter body 12 terminates at the distal end thereof in tip electrode 24. Electrode 26, in the form of a conductive peripheral band together with tip electrode 24 constitute one electrode pair. Another electrode 28, similar in configuration to electrode 26, is one member of the next 10 adjacent electrode pair. Situated therebetween, i.e., between paired electrodes 24, 26 and paired electrodes 28, 30, is emissive face 36 of fiber optic 40 (FIG. 3). The positioning of the emissive faces of the fiber optics between electrode pairs permits a precise location of the foci of the tachyarrhythmias.

Alongside fiber optic 40 is optional irrigation conduit 42 that defines flushing channel 44 for dispensing an irrigation liquid, such as physiological saline, or the like, during the medical procedure. Both fiber optic 40 and irrigation conduit 42 are embedded in an epoxy resin compound 46 or the like retaining means contained within side boss 48. Irrigation via the flushing channel helps to keep the emissive face of the fiber optic free of debris during use. The irrigating liquid also cools the tissue and minimizes the likelihood of tissue charring during the lasing procedure.

Optional fiber optic 52 having emissive face 50 as well as irrigation conduit 53 contiguous therewith and defining auxiliary flushing channel 54 can be provided also in tip electrode 24, if desired. Tip electrode 24 and electrodes 26 and 28 are each provided with respective signal transmitting leads or wires 64, 66 and 68 that are connected to appropriate monitoring and mapping instrumentation by means of connector plug 18 shown in FIG. 1.

Distal end region 16 further includes catheter directing ribbon 58 and tip deflecting wire 60.

Tip electrode 24 is usually metallic and, in addition to being used for mapping, can also be used to deliver radio frequency (RE) energy, or direct current (DC) to effect tissue ablation in addition to the tissue ablation effected by laser energy delivered by means of 10 fiber optics 36 and 52. Electrodes 26 and 28 can be metallic bands or conductive polymers, as desired and as expedient.

Figure 4:
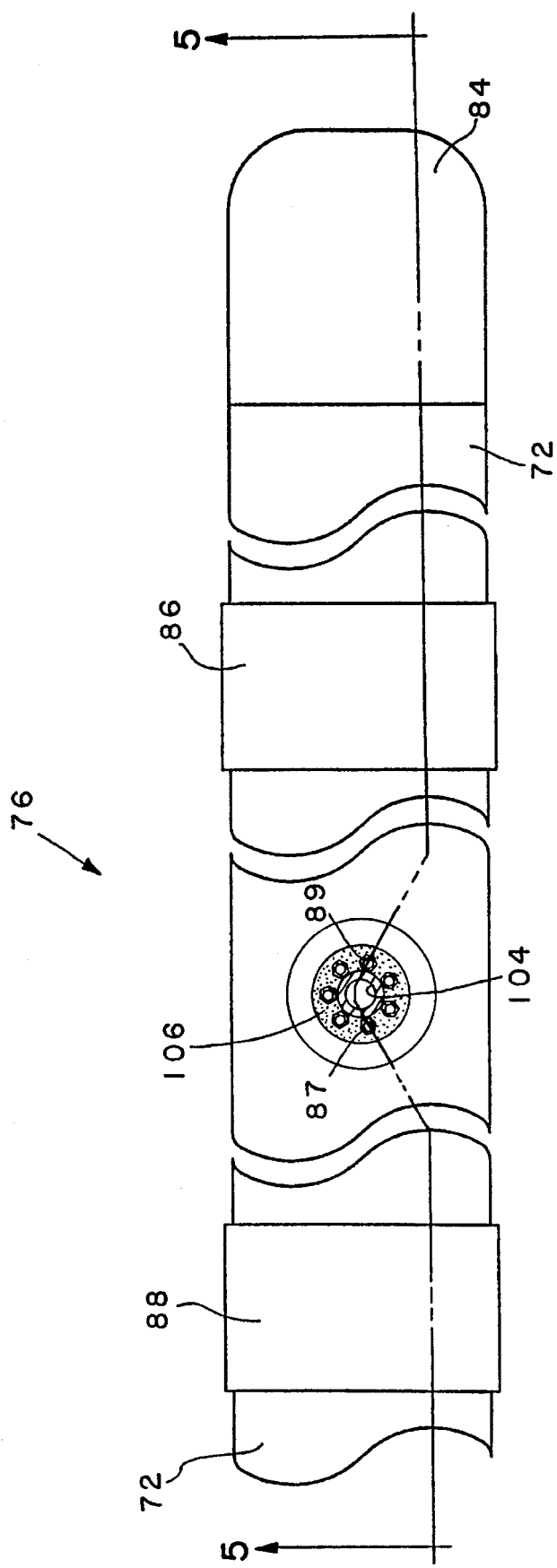
FIG. 4 is an enlarged fragmentary view similar to FIG. 2 but showing an alternate embodiment of the present invention.
Figure 5:
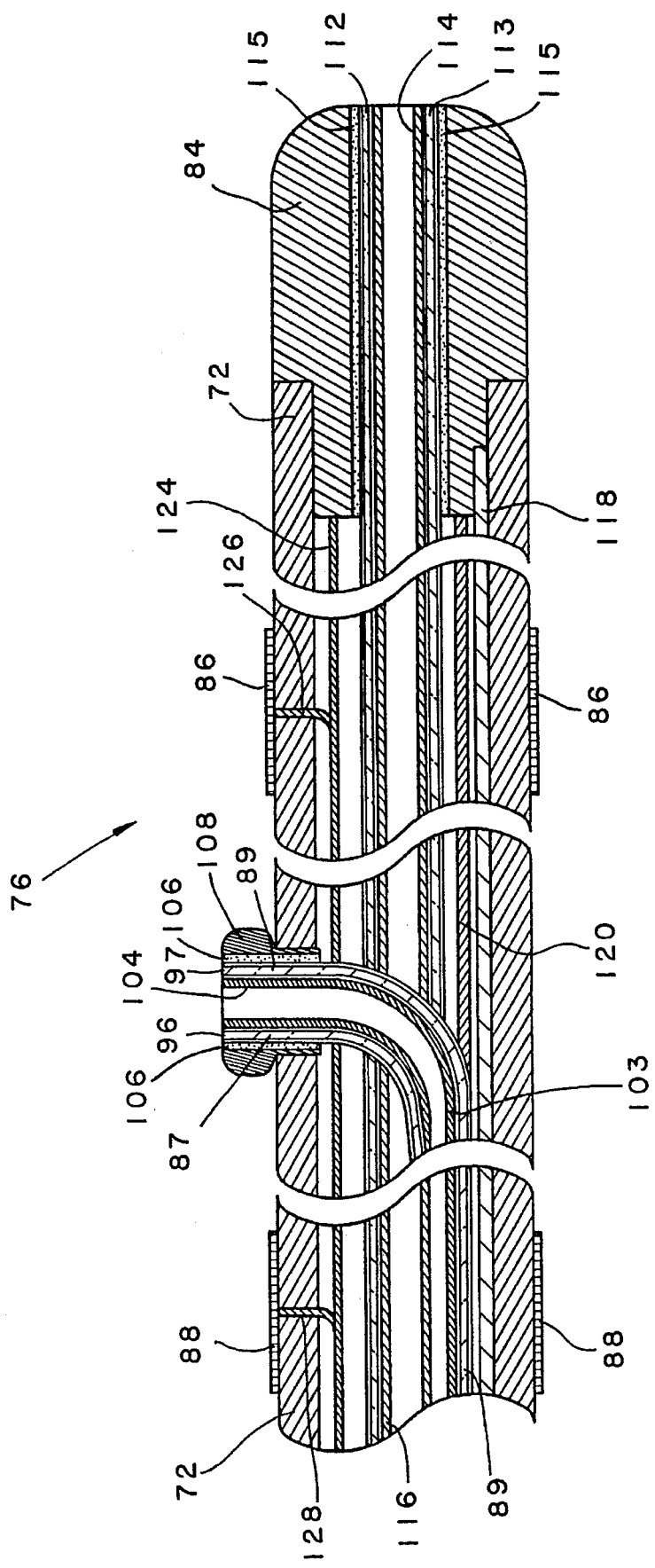
FIG. 5 is a sectional elevation taking alone plane 5—5 in FIG. 4.

An alternate catheter design is shown in FIGS. 4 and 5 where distal end region 76 is provided with plural fiber optics between each mapping electrode pair. In particular, the distal end of catheter body 72 terminates in tip electrode 84. Electrode 86 together with tip electrode 84 form a pair of mapping electrodes. Electrode 88 is one member of another pair of mapping electrodes carried on the surface of catheter body 72.

Situated between electrodes 86 and 88 are seven fiber optics such as 87 and 89 with respective emissive end faces 96 and 97 that surround the outlet port of flushing lumen 104 defined by irrigation conduit 103. The fiber optics as well as irrigation conduit 103 are embedded in epoxy resin compound 106 contained within boss 108. Signal wires 124, 126 and 128 for transmission of electrical signals are operably connected to respective electrodes 84, 86 and 88.

Distal end region 76 is also provided with substantially co-axial irrigation conduit 116 that defines flushing lumen 114. Irrigation conduit 116 is likewise surrounded by plural fiber optics such as 112 and 113 embedded in epoxy resin compound 115. Manipulation of catheter distal end region 76 is effected by means of directing ribbon 118 and deflecting wire 120.

Figure 6:
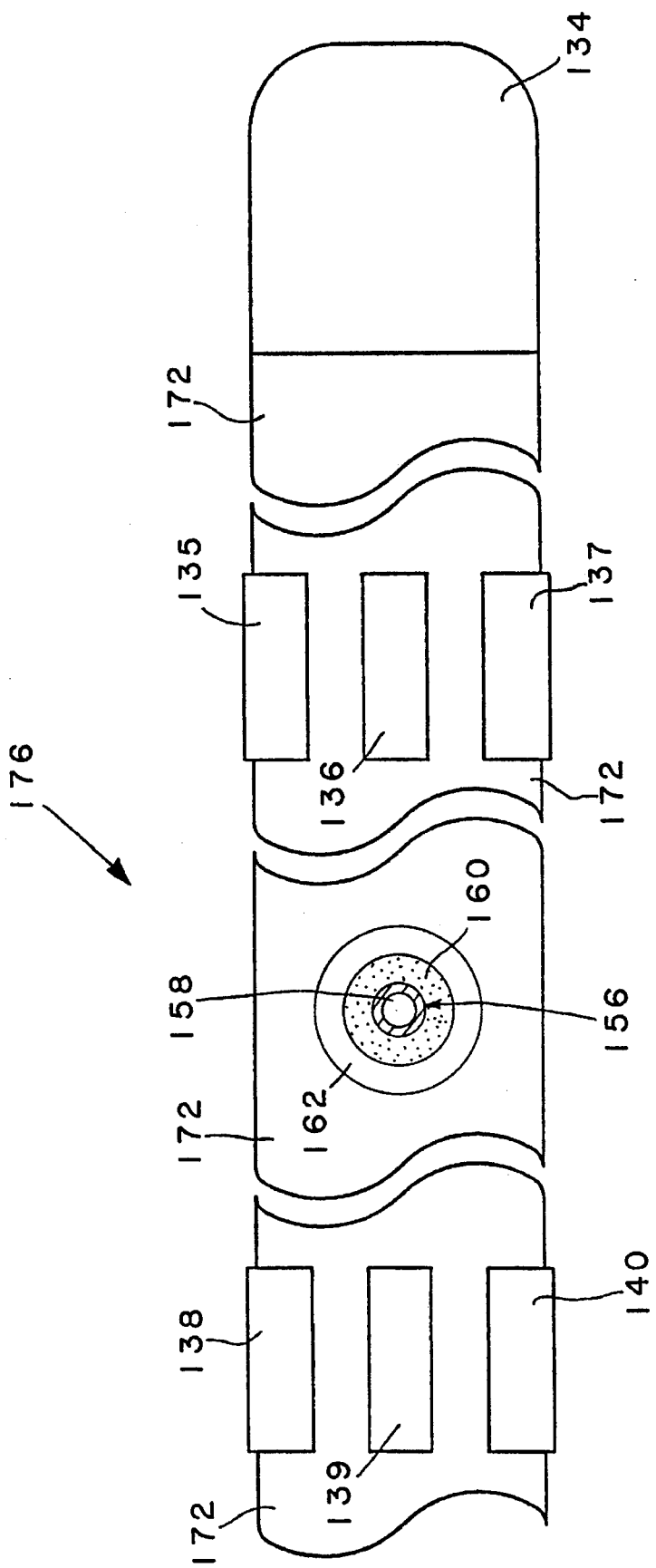
FIG. 6 is an enlarged fragmentary view of a distal end region of a mapping and lasing catheter showing yet another embodiment of the present invention.

Mapping electrodes such as electrodes 26 and 28 shown in FIGS. 2 and 3, or electrodes 86 and 88 shown in FIGS. 4 and 5, need not be continuous peripheral bands. Instead, the electrode pairs can be constituted by paired conductive lands or regions such as those illustrated in FIG. 6 for mapping and lasing catheter distal end region 176. Surface electrodes such as 135, 136 and 137 surround catheter body 172 at a location adjacent to tip electrode 134. A mapping electrode pair can be formed by one or more of electrodes 135–137 and tip electrode 134. Alternatively, mapping electrode pairs can be formed as well among the peripheral array of electrodes such as 135–137. Another array of mapping electrodes is illustrated by surface electrodes 138, 139, 140 that can be suitably interconnected to provide paired mapping electrodes among themselves or with a similar peripheral array of electrodes (not shown) spaced therefrom in the direction away from tip electrode 134 and toward the catheter proximal end.

Fiber optic 156 is positioned between paired electrode arrays 135–137 and 138–140 so that emissive end face 158 of fiber optic 156 can emit a direct laser beam substantially laterally, i.e., in a direction substantially normal to the longitudinal axis of catheter body 172. Fiber optic 156 is embedded in epoxy resin compound 160 and retained in a fixed position relative to catheter body 172 by side boss 162. Each of the electrodes is provided with an appropriately operably associated wire or lead for mapping and/or monitoring purposes in the same manner as hereinbefore described in connection with FIGS. 2–5.

The size of the present mapping and lasing catheter can vary. However, usually the mapping and lasing catheter has a diameter in the range of about 4 French (1.35 millimeters) to about 10 French (3.3 millimeters). Preferably, the present mapping and lasing catheters have a diameter in the range of about 6 French (2 millimeters) to about 7 French (2.3 millimeters).

The spacing of electrode pairs can vary, depending upon the size of the catheter and the desired mapping. Preferably, electrode pairs are spaced at least about one millimeter from one another but no more than about 10 millimeters from one another.

Any laser may be utilized for tissue ablation by means of the present catheter as long as the laser can be transmitted along the fiber optics in the catheter. The choice of a particular laser wavelength is also influenced in part by the desired depth of tissue penetration during ablation. The relatively deeper tissue penetration of neodymium-doped yttrium-aluminum-garnet (Nd:YAG) laser is preferred, while for a relatively shallower tissue penetration an excimer laser can be used. Intermediate depth tissue penetration can be achieved with argon and holmium-doped yttrium-aluminum-garnet (Ho:YAG) lasers. Pulsed as well as continuous wave (CW) lasers can be utilized for the present purposes.

The duration of the pulses and the amount of laser power and energy to be employed depends upon a number of factors, such as the type of laser being employed, the nature of the disease, the location and nature of the heart tissue being treated, whether the tissue is normal or diseased, and the nature of the adjoining tissue structure. With an argon laser, the pulse duration may vary over the range of from about $\frac{1}{10}$ to about 5 seconds, the power employed may be in the range of from about 2 to about 50 watts, and the energy delivered per site may be in the range of from about 10 to about 1000 Joules. For example, for superficial vaporization of tissue in the atrium or the area of the AV conduction system, pulse durations in the range of from about 0.3 to about 0.5 seconds, laser power in the range of from about 3 to 5 watts, and energy in the range of from about 10 to about 200 Joules per site, may be employed. However, for incising a ventricle wall or creating focal lesions in ventricular tissue, pulse durations in the range of from about one to about two seconds, power in the range of from about 8 to about 10 watts, and energy in the range of from about 100 to about 1000 Joules per site, are suitable. For Nd:YAG lasers, pulse duration as long as about 20seconds has been used to ablate heart tissue. The pulse duration for a krypton fluoride excimer laser is much shorter, usually by a factor of 100 or 1000, relative to the pulse duration for an argon laser. Commercially available laser generators often have a timer apparatus which permits the setting, and changing of the setting, of the pulse duration as well as of the intervals between the pulses. The intervals between the discrete pulses of laser energy is of lesser importance, and can be in the range of about 0.01 to about 30 seconds, preferably in the range of about 0.5 to about 5 seconds.

The laser energy literally vaporizes the heart tissue to which it is directed. The focal lesions which are created by the pulses of laser energy are relatively shallow craters or cylindrical recesses in the tissue of the heart, rather like shallow miniature post holes. The lesions are preferably about two to three millimeters deep. Their diameters are a function partially of the diameter of the incident laser beam with which they are created, partially of the type of tissue, and partially of whether the tissue is normal or diseased. The desired lesion diameter depends on the location in the heart where the lesions are being created. For instance, relatively smaller lesion diameters are preferred near the AV node, whereas relatively larger lesion diameters are formed when ablating ventricle tissue.

The tissue area in which focal lesions are to be created varies, depending upon the nature and extent of the tachyarrhythmia which is occurring. Occasionally the area is rather small, of the order of a few square centimeters, but sometimes the area is much larger, such as 20 square centimeters. It is preferred to create the lesions in some form of a pattern, with the distance between the center lines of the lesions being in the range of about 2 to about 50 millimeters.

The minimum effective, the maximum permissible, and the optimum, of the several process variables referred to herein (e.g., type and power of the laser, energy per site, diameter of the optical fiber, pulse duration, and the diameter, depth and spacing of the focal lesions) may vary from human patient to human patient, depending upon many factors, including illustratively the nature and severity of the tachyarrhythmia, its location, the nature of the tissue at and adjacent to a site of ablation, and the general physical condition of a specific patient. This lack of uniformity, typical in medical science, precludes precise quantitative statements of the ranges of physical parameters uniformly applicable to all human patients under all conditions. These physical parameters can be readily arrived at by those skilled in the art, however.

Pulsed laser ablation processes have several advantages. They are applicable for use on the tissues of any portion of the heart where the source of a tachyarrhythmia may be located, in contrast to other means of ablation of tissue. They are efficacious in all such locations. They produce a virtually bloodless incision, which is of importance in heart surgery. Such processes create a focal lesion, or an incision, in which there is less carbonization or charring of tissue as well as less coagulation, and in which the extent of tissue damage, measured radially outwardly by histological studies and by impairment of normal electrical activity of the heart tissue, is less than with a continuous or a sequential continuous laser beam, or with electrical ablation processes. There is less risk of inadvertent perforation of tissue as compared to the use of a continuous laser system or a laser system requiring relatively high power. There is also less risk of damage to the distal tip of the optical fiber, which, should it occur, decreases the uniformity of the effect on the tissue of the laser beam, and requires more frequent intraoperative changes of the apparatus comprising the optical fiber.

In use, the mapping and lasing catheter is inserted using standard cardiac catheterization techniques. Pre-ablation mapping is performed to localize the arrhythmogenic region. This can include localization of sinus node, atrial, atrioventricular (AV) node, selective AV nodal pathways (fast and slow), Bundle of His, strioventricular bypass tracts and ventricular tissues. Relatively high density electrode arrays are particularly desirable for mapping in preparation for atrial or ventricular ablation. For ventricular ablation both right and left ventricular sites can be mapped. Usually five major zones in the right ventricle and twenty zones in the left ventricle are initially mapped. Typical target markers can include early, mid or late diastolic electrical activity during tachycardia, late potentials during sinus or other rhythms, earliest activation sites, entrainment of slow conduction zones, pace mapping selections or zones that can exhibit tachycardia modification during test ablative pulses. Similar markers for other reentrant arrhythmias could include pathway potentials for the AV node or by pass tracts, slow conduction or early activation zones during atrial flutter, or even sinus node potentials.

For ventricular tachycardia, the active site, defined in electrical activation terms, encompasses a window of electrical activation time within the electrical diastole of the heart, i.e., about 20 to about 80 percent, preferably about 35 to about 50 percent, of the time period of the diastolic interval. For treating ventricular tachycardia it is preferred to continuously monitor the electrical activation time within the electrical diastole during laser ablation of the heart tissue.

For left ventricular mapping a large U-shaped loop with the catheter tip in the antero-basal segment of the left ventricle is progressively withdrawn to map all the segments of the right anterior oblique view of the left ventricle. The catheter can then be swung posteriorly under the mitral valve to map the posterior, inferior and infero-apical regions. Finally the catheter can be withdrawn along the left ventricular septum to the aortic root to map the entire long axis of the septum, if desired. The deflecting tip of the catheter is used to maneuver the catheter electrode arrays to different ventricular endocardial locations. The target tissue of interest for arrhythmogenesis also can be localized by epicardial sock mapping or endocardial balloon mapping, or by both methods. The laser catheter can be inserted by atriotomy or ventriculotomy, or by other vascular access for endocardial ablation or under direct vision for epicardial application. Ablation can be performed during normothermia and during induced tachycardia to directly evaluate its efficacy. Other catheter techniques are known and are available for mapping the specialized conduction system and the atrioventricular annulus, right or left atria or coronary sinus. Mixed epicardial and endocardial approaches may also be utilized with more than one catheter being employed.

The foregoing specification is intended to be illustrative of the present invention and is not to be taken as limiting. Still other variations and rearrangements of parts within the spirit and scope of this invention are possible and will readily present themselves to those skilled in the art.

We claim:

1. A continuous mapping and lasing catheter, suitable for intraoperative and percutaneous application, comprising a tubular body having at a distal end region thereof an envelope of plural surface electrode pairs spaced from one another and at least one fiber optic within said envelope for directing a laser beam at a target site adjacent to said envelope; said fiber optic being positioned between adjacent electrode pairs.

2. The mapping and lasing catheter in accordance with claim 1 wherein the electrode pairs are spaced at least about 1 millimeter from one another but no more than about 10 millimeters from one another.

3. The mapping and lasing catheter in accordance with claim 1 wherein plural fiber optics are situated within said envelope.

4. The mapping and lasing catheter in accordance with claim 1 wherein plural fiber optics are situated between adjacent electrode pairs.

5. The mapping and lasing catheter in accordance with claim 1 wherein a flushing channel is defined by the tubular body and terminates in an outlet port between adjacent electrode pairs.

6. The mapping and lasing catheter in accordance with claim 5 wherein the outlet port of said flushing channel is surrounded by fiber optics.

7. The mapping and lasing catheter in accordance with claim 1 wherein said envelope has an outside diameter in the range of about 4 French to about 10 French.

8. The mapping and lasing catheter in accordance with claim 1 wherein said envelope has an outside diameter in the range of about 6 French to about 7 French.

9. A continuous mapping and lasing catheter comprising:

a flexible tubular body configured to house at least one fiber optic, and having a distal region and an exterior surface;

at least two electrode pairs disposed in association with the distal region and the exterior surface; and at least one fiber optic housed in the tubular body with an emissive face of the fiber optic situated between electrode pairs to provide a laser beam between the two electrode pairs.

10. The mapping and lasing catheter in accordance with claim 9 wherein the fiber optic terminates at the exterior surface and the distal region.

11. The mapping and lasing catheter in accordance with claim 9 further including a plurality of fiber optics to provide a laser beam at the distal region between the two electrode pairs.

12. The mapping and lasing catheter in accordance with claim 9 wherein the electrode pairs are continuous bands that circumscribe the tubular body.

13. The mapping and lasing catheter in accordance with claim 9 wherein the electrode pairs are discontinuous lands.

14. The mapping and lasing catheter in accordance with claim 9 wherein the fiber optic includes an end face positioned so that upon deflection of the distal region the end face remains on an outer curvature of a resulting bend of the distal region.

15. The mapping and lasing catheter in accordance with claim 9 wherein the tubular body further defines an irrigation conduit associated with the fiber optic.

16. The mapping and lasing catheter in accordance with claim 11 further comprising a tip electrode and wherein the tubular body includes a tip at which the tip electrode is located.

17. The mapping and lasing catheter in accordance with claim 16 further including within the tubular body another fiber optic to provide a laser beam substantially normal to a longitudinal axis of the tubular body.

* * * * *